(12) United States Patent
Johnston et al.

(10) Patent No.: US 9,408,718 B2
(45) Date of Patent: Aug. 9, 2016

(54) INTER-VERTEBRAL IMPLANT WITH ANGLED PLATE

(75) Inventors: Terry Johnston, San Carlos, CA (US); Fred H. Geisler, Aurora, IL (US)

(73) Assignee: RHAUSLER, INC., San Carlos, CA (US)

( * ) Notice: Subject to any disclaimer, the term of this patent is extended or adjusted under 35 U.S.C. 154(b) by 0 days.

(21) Appl. No.: 13/538,039

(22) Filed: Jun. 29, 2012

(65) Prior Publication Data

US 2012/0316649 A1    Dec. 13, 2012

Related U.S. Application Data

(63) Continuation-in-part of application No. 12/650,600, filed on Dec. 31, 2009, now Pat. No. 8,945,226.

(51) Int. Cl.
*A61F 2/44* (2006.01)
*A61F 2/28* (2006.01)
*A61F 2/30* (2006.01)

(52) U.S. Cl.
CPC ............ *A61F 2/447* (2013.01); *A61F 2/442* (2013.01); *A61F 2002/2817* (2013.01); *A61F 2002/2835* (2013.01); *A61F 2002/3008* (2013.01); *A61F 2002/30056* (2013.01); *A61F 2002/30271* (2013.01); *A61F 2002/30448* (2013.01); *A61F 2002/30576* (2013.01);
(Continued)

(58) Field of Classification Search
CPC ........ A61F 2/447; A61F 2/44; A61F 2/4455; A61F 2/446; A61F 2/4465; A61F 2002/4475; A61F 2002/448; A61F 2002/4485; A61F 2002/449; A61B 17/7059

USPC ............................. 623/17.11–17.16; 606/912
See application file for complete search history.

(56) References Cited

U.S. PATENT DOCUMENTS

| | | |
|---|---|---|
| 5,425,772 A | 6/1995 | Brantigan |
| 5,766,252 A | 6/1998 | Henry et al. |

(Continued)

FOREIGN PATENT DOCUMENTS

| | | |
|---|---|---|
| EP | 18472040 A1 | 10/2007 |
| WO | 2007038545 A1 | 4/2007 |
| WO | 2008154326 A1 | 12/2008 |

OTHER PUBLICATIONS

International Search Report and Written Opinion and related PCT/US2011/020053, dated Sep. 22, 2011.
(Continued)

*Primary Examiner* — Christian Sevilla
*Assistant Examiner* — Eric S Gibson
(74) *Attorney, Agent, or Firm* — Kramer Amado, P.C.

(57) ABSTRACT

An inter-vertebral implant having a hollow frame having a top load bearing surface and a bottom load bearing surface may be inserted between a first spinal vertebra and a second spinal vertebra. The top load bearing surface and the bottom load bearing surface may each include an opening allowing access to the interior of the frame. A front surface may extend between the top load bearing surface and the bottom load bearing surface, and a rear surface may extend between the top load bearing surface and the bottom load bearing surface. A plate is attached to the front surface of the support device. The interior front plate may be arranged along a plane (P), and an axis (A) between the top load bearing surface and the bottom load bearing surface may be at a non-right angle relative to the plane (P).

27 Claims, 10 Drawing Sheets

(52) U.S. Cl.
CPC ............. *A61F 2002/30578* (2013.01); *A61F 2002/30604* (2013.01); *A61F 2002/30774* (2013.01); *A61F 2002/30777* (2013.01); *A61F 2002/30787* (2013.01); *A61F 2002/30789* (2013.01); *A61F 2002/30904* (2013.01); *A61F 2002/30906* (2013.01); *A61F 2002/30925* (2013.01); *A61F 2002/30927* (2013.01); *A61F 2002/4475* (2013.01); *A61F 2310/00023* (2013.01); *A61F 2310/00047* (2013.01); *A61F 2310/00053* (2013.01); *A61F 2310/00071* (2013.01); *A61F 2310/00203* (2013.01); *A61F 2310/00221* (2013.01); *A61F 2310/00239* (2013.01); *A61F 2310/00293* (2013.01); *A61F 2310/00796* (2013.01)

(56) References Cited

U.S. PATENT DOCUMENTS

| | | | |
|---|---|---|---|
| 6,231,610 B1 | 5/2001 | Geisler | |
| 6,454,805 B1 | 9/2002 | Baccelli et al. | |
| 6,629,998 B1 | 10/2003 | Lin | |
| 6,635,086 B2 | 10/2003 | Lin | |
| 6,736,849 B2* | 5/2004 | Li et al. | 623/17.11 |
| 7,182,784 B2* | 2/2007 | Evans et al. | 623/17.15 |
| 7,232,464 B2* | 6/2007 | Mathieu et al. | 623/17.11 |
| 7,238,186 B2 | 7/2007 | Zdeblick | |
| 7,238,203 B2 | 7/2007 | Bagga | |
| 7,255,710 B2* | 8/2007 | White et al. | 623/1.15 |
| 7,491,237 B2* | 2/2009 | Randall et al. | 623/17.11 |
| 7,494,507 B2* | 2/2009 | Dixon et al. | 623/17.14 |
| 7,621,956 B2* | 11/2009 | Paul et al. | 623/17.15 |
| 7,937,952 B2* | 5/2011 | Johnson | 62/3.2 |
| 8,496,708 B2* | 7/2013 | Blain | 623/17.16 |
| 8,613,772 B2* | 12/2013 | Bray et al. | 623/17.16 |
| 2001/0012966 A1* | 8/2001 | Studer et al. | 623/17.16 |
| 2003/0028249 A1 | 2/2003 | Baccelli et al. | |
| 2003/0065393 A1 | 4/2003 | Moumene et al. | |
| 2005/0177236 A1 | 8/2005 | Mathieu | |
| 2005/0177245 A1* | 8/2005 | Leatherbury et al. | 623/23.5 |
| 2005/0187625 A1 | 8/2005 | Wolek et al. | |
| 2005/0216082 A1 | 9/2005 | Wilson et al. | |
| 2007/0250167 A1* | 10/2007 | Bray et al. | 623/17.11 |
| 2007/0255416 A1 | 11/2007 | Melkent | |
| 2008/0071372 A1 | 3/2008 | Butler et al. | |
| 2008/0177307 A1 | 7/2008 | Moskowitz et al. | |
| 2008/0243252 A1 | 10/2008 | Hansen | |
| 2008/0281424 A1* | 11/2008 | Parry et al. | 623/17.16 |
| 2008/0312742 A1 | 12/2008 | Abernathie | |
| 2009/0105824 A1 | 4/2009 | Jones | |
| 2009/0105825 A1 | 4/2009 | Foreman | |
| 2009/0326580 A1* | 12/2009 | Anderson et al. | 606/246 |

OTHER PUBLICATIONS

Supplementary European Search Report to EP 11728551; dated Jul. 9, 2013.

* cited by examiner

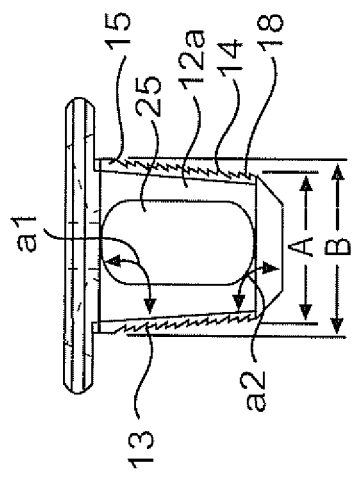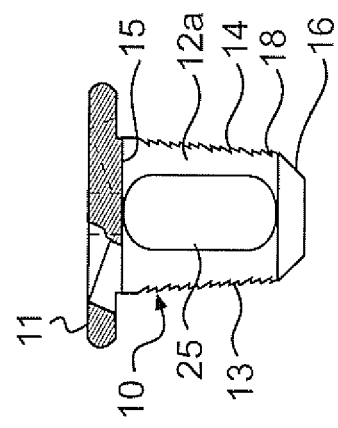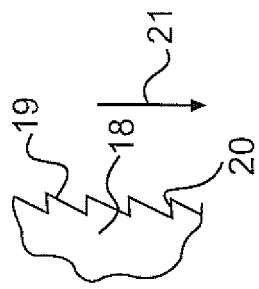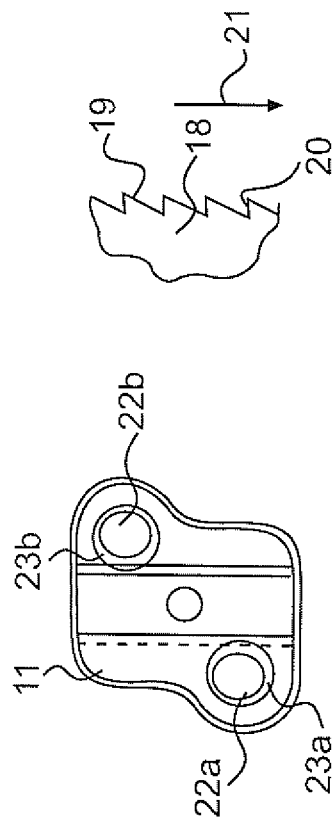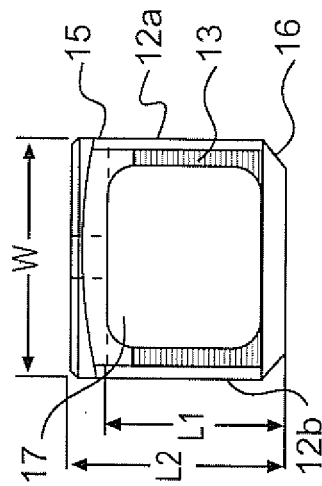

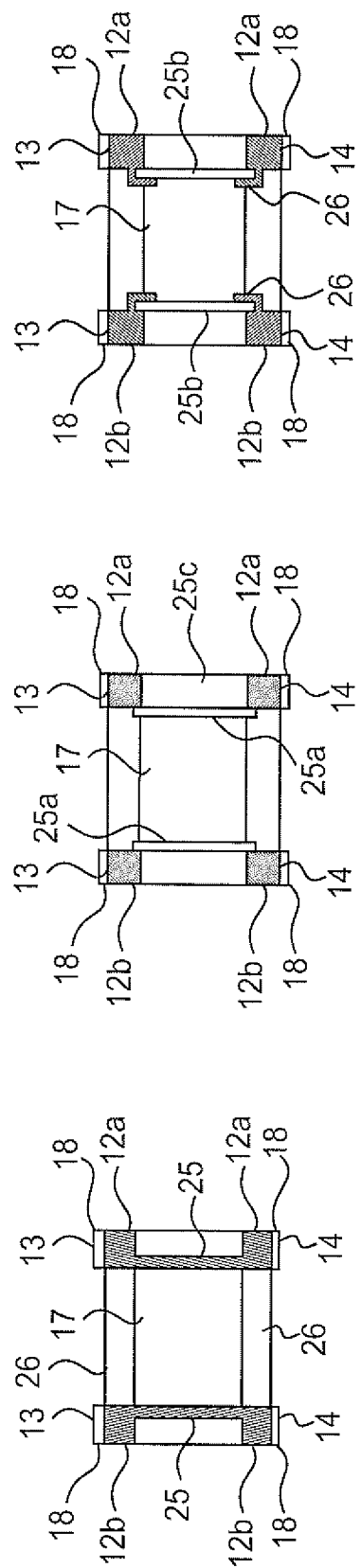

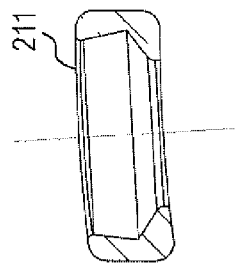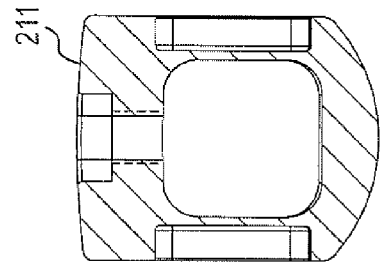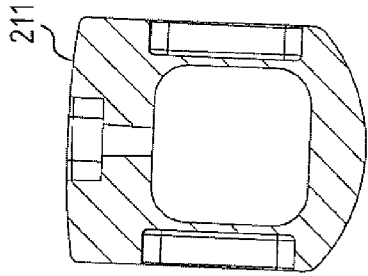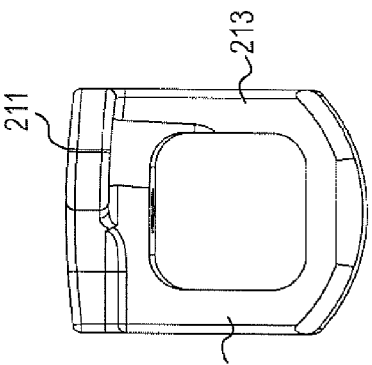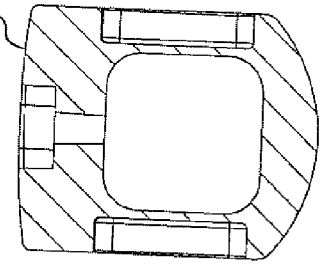

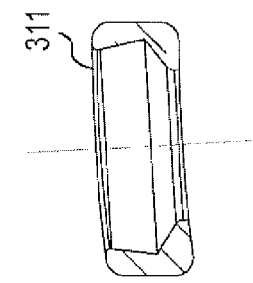
FIG. 26
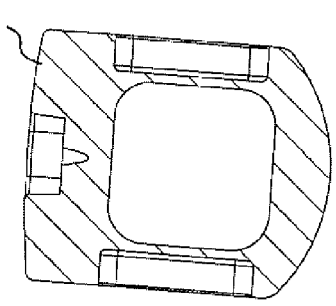
FIG. 29
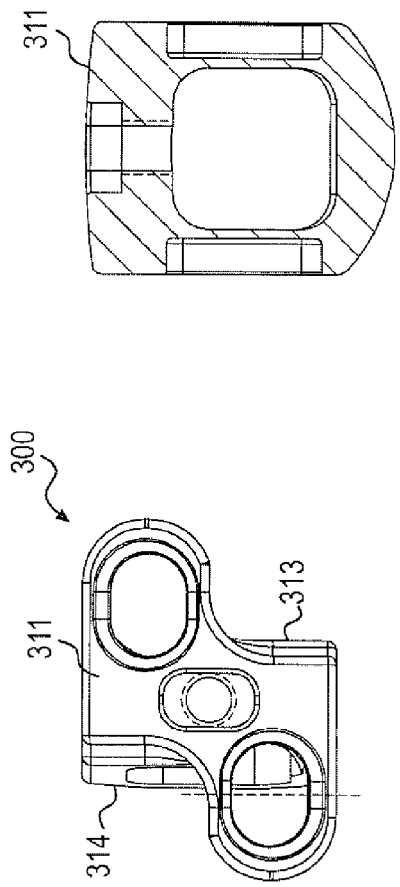
FIG. 25
FIG. 28
FIG. 24
FIG. 27

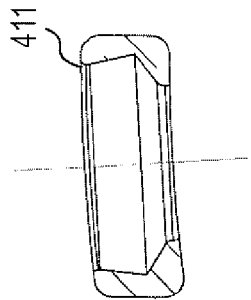
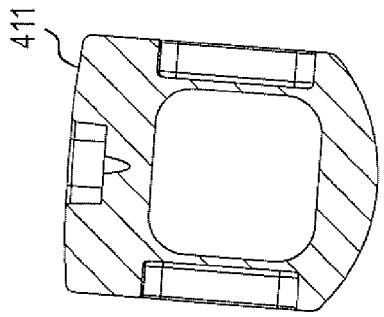
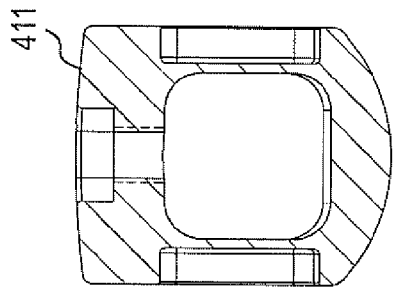
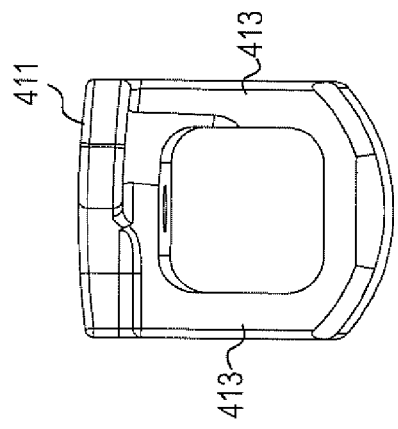
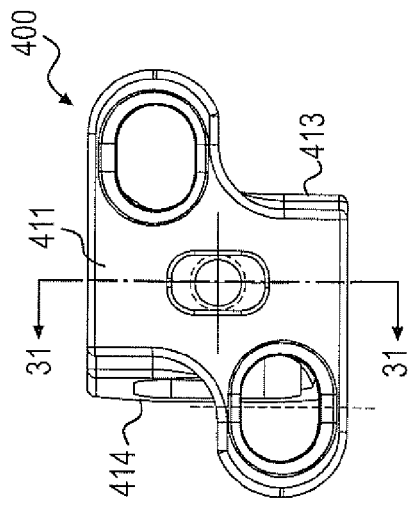
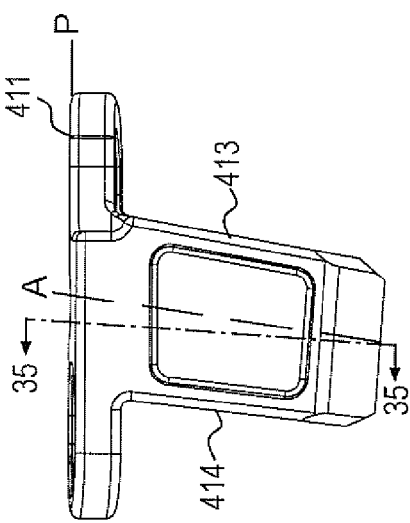

INTER-VERTEBRAL IMPLANT WITH ANGLED PLATE

CROSS REFERENCE TO RELATED APPLICATIONS

This application is a continuation-in-part of U.S. patent application Ser. No. 12/650,600 entitled "Cervical Spacer", filed on Dec. 31, 2009 and currently pending. The entire disclosure of U.S. patent application Ser. No. 12/650,600 which was published as U.S. Patent Publication No. 2011-0160860 AI on Jun. 30, 2011 is hereby incorporated by reference in its entirety.

BACKGROUND

The present invention relates to spinal column spacers.

The human spinal column consists of 33 (sometimes 34) vertebrae divided into five groups: cervical, thoracic, lumbar, sacral and coccygeal vertebrae areas. The sacral vertebrae are fused into a single bone as is the coccygeal vertebrae, usually designated as the coccyx. The movable vertebrae are found in the cervical, thoracic and lumbar areas. Each area has a characteristic curve. Thus, various vertebrae differ in size and shape depending on their location in the spinal column.

Spacers exist for repairing the spinal column. Most of the known spacers are designed for the lumbar or thoracic regions of the spine. Since the lumbar or thoracic vertebrae are structurally different from the cervical vertebrae, spacers designed for the lumbar or thoracic region will not perform properly in the cervical region. Most devices used clinically for repairing the anterior cervical area of the spine usually involve some elements of screw, plate, and spacers for bony attachment and/or support.

Various prior art cervical spacers are known. These devices may be made from X-ray transparent materials or from X-ray opaque materials. Devices made from X-ray transparent materials typically are, as the name implies, difficult to see on routine radiographic X-ray studies. Although they may be visualized on expensive CT scans with a much high patient radiation dose, these spacers still cannot be seen directly on plain radiographic images that are routinely used for follow up examination and monitoring of the bony healing and alignment. It has been proposed to solve this imaging problem by adding dots or spots of X-ray opaque markers to the spacers. However the position of the spacer must be inferred on the basis of these markers, generally leaving some ambiguity of the exact position of all of the edges. Devices made from X-ray opaque materials, on the other hand, can be seen on X-ray, but the opaqueness often makes it difficult to assess the status of healing grafting material inside the spacer, and in some cases difficult to assess the position of the attaching screws of the construct. One method directed to solving this problem is a skeletal frame that is opaque to X-rays, but, because of being a skeletal structure, has openings that allow X-ray passage and therefore permit the doctor to view the interior of the spacer. Specifically, these spacers employ a skeletal frame of a material such as titanium, the skeletal form providing multiple openings allowing X-ray visualization of the interior of the spacer. Regarding the known designs for cervical spacers, these represent the state of the art that strives to meet two important performance criteria: strength, increased by the titanium frame, and X-ray transparency, provided by the multiple openings of the skeletal frame.

The present inventors have identified, however, that this state-of-the-art cervical spacer, constructed with a skeletal form, regardless of the specific shape of the skeletal form, must arrange and dimension the skeletal member to proved windows or openings large enough to enable viewing of the interior of the skeletal form by X-ray. These windows allow the doctor to monitor the process of as the surgical arthrodesis heals to a mature fusion between the upper and lower vertebrae. However, it is inherent to a skeletal structure cervical spacer that these windows or openings cannot be enlarged formed without sacrificing strength of the device. Simply put, to make the openings larger there are two options: make the skeletal members with a smaller diameter, or use fewer skeletal members. Both of these decrease strength Various embodiments of the disclosed invention solve these long-felt needs for practical stabilization of the cervical vertebrae and offer additional features and benefits, such as, for example, significantly increased strength to the spacer while maintaining sufficient X-ray transparency or translucency to enable proper follow-up monitoring with conventional X-ray methods.

SUMMARY

In light of the long-felt need for strong cervical spacers which do not impede X-ray observation of the site of implantation, a brief summary of various examples of one embodiment is presented. Some simplifications and omissions may be made in the following summary as it is intended to highlight and introduce some aspects of the various examples of one embodiment, not to limit the scope of the disclosure. Detailed descriptions of an illustrative exemplary embodiments that will further assist those of ordinary skill in the art to make and use the disclosed subject matter will follow in later sections.

The applications of the disclosed embodiments generally relate to other applications may be understood by persons of ordinary skills in the art, though, upon reading this disclosure an anterior cervical spinal column support. One example comprises a unique hollow prism-shaped frame arranged and diminished to fit between and stabilize cervical vertebrae. This and other examples provide spacing and support where, for example, the intervertebral disc has failed due to a slipped, herniated or ruptured disc. Because of the nature of degenerative disease in the cervical area, typically the example embodiments are used after a one or two level anterior cervical discectomy in degenerative disc disease where fusion and internal stabilization is desired. In more severe cases of cervical degenerative disease three or four levels may be stabilized. One among the features and benefits of various example embodiments is the provision of mechanical stabilization against bending. Another among the features and benefits of the various example embodiments is the correction of loss of normal lordosis angle and disc space height loss that commonly accompanies the degenerative disc disease. Another feature and benefit of the various example embodiments is the provision of a hollow space within the support configured to hold a bone graft, or any other type of bone grafting material. One further feature and benefit of the various example embodiments is the elimination of escape of grafting materials from the interior of the spacer.

Various examples according to one embodiment provide an implantable spacer that performs as an anterior cervical column support device.

Examples according to one embodiment provide an anterior cervical column support device for insertion between a first spinal vertebra and a second spinal vertebra, comprising a hollow frame, preferably a hollow prism-shaped frame, more preferably a hollow right prism-shaped frame, having a top load bearing surface and a bottom load bearing surface.

The top load bearing surface and the bottom load bearing surface each include an opening allowing access to the interior of the frame. For example, grafting material may be inserted into the interior of the frame through one or both of the openings in the top load bearing surface and the bottom load bearing surface. The prism-shaped frame also includes a front surface that is relatively opaque to X-rays, attached between the top load bearing surface and the bottom load bearing surface; and a rear surface that is relatively opaque to X-rays attached between the top load bearing surface and the bottom load bearing surface. Two side surfaces are attached between the front surface and the rear surface, each side surface comprising a solid side panel which is at least X-ray translucent. An anterior plate portion attached to the front surface of the support device may include a plurality of holes for receiving a plurality of fasteners for holding the anterior plate in position. In such an example, these holes for medical fasteners may be indented offset screw holes, and may receive screws for securing the anterior plate portion to the upper and lower vertebrae. In various examples of one embodiment, one screw hole directs a screw toward the first vertebra, and the other screw hole directs a screw toward the second vertebra. This high frictional surface can have osteointegration properties so that rapid bony healing next to this surface forms a bone-metal adhesion to aid in long term stability and enhances bony healing in the enter of the cage portion by this rapidly obtained immobilization/stability.

According to at least one exemplary embodiment of the anterior cervical column support device a top load bearing surface includes a high friction surface for increasing frictional forces between the top load bearing surface and the first vertebrae; while various examples of one embodiment of the bottom load bearing surface include a high friction surface for increasing frictional forces between the bottom load bearing surface and the second vertebrae. Roughening of the surface by sandblasting or etching may also serve to increase frictional forces. Methods of microscopically roughening the implant at the implant-bone interface surface through etching or sandblasting also serve to enhance bony ingrowth and adhesion.

According to one aspect, the high friction surface for increasing frictional forces between the top load bearing surface and the first vertebrae may include serrations for increasing frictional forces between the bottom load bearing surface and the second vertebrae. According to one aspect, high friction surface for increasing frictional forces between the bottom load bearing surface and the second vertebrae may include serrations for increasing frictional forces between the bottom load bearing surface and the second vertebrae.

According to one aspect of various examples of one embodiment, the high friction surface for increasing frictional forces between the load bearing surfaces and adjacent bone surfaces may be formed by roughening the top and bottom load bearing surfaces. Roughening the top and bottom load bearing surfaces may be done by, for example, etching the top and bottom load bearing surfaces or sandblasting the top and bottom load bearing surfaces.

According to one particular aspect of various examples of one embodiment, an anterior cervical column support device includes solid side panels, and each solid side panel may be an X-ray transparent or X-ray translucent thickness of a defined material. As will be described in greater detail in later sections, the thickness of the solid panel is readily selected based on this disclosure, as a thickness value at which the sidewall provides appreciable structural strength, yet provides sufficiently X-ray transparency or X-ray translucency to allow the physician an adequate view of the interior space, using only conventional X-ray. As one illustrative example, a titanium sheet or foil which is 0.1 to 0.3 mm thick is X-ray transparent or translucent, to enable visibility using conventional X-ray equipment and is sufficiently thick to impact significant added strength, and may therefore be used as a solid side panel. Similarly, an aluminum sheet may be employed by choosing its thickness to meet both the strength and the X-ray transparent features. In certain embodiments, each solid side panel is attached between the front surface and the rear surface of the anterior cervical column support device, and is also attached between the top load bearing surface and the bottom load bearing surface.

As described above, in examples according to certain embodiments, each solid side panel may be, for example, a titanium material between approximately 0.1 mm thick and 0.3 mm thick and in such embodiments, the solid side panels increase the strength of the cervical column support device by a factor of at least two, as compared to a comparative skeletal frame cervical column support device.

According to at least one exemplary embodiment, the vertical distance between the top load bearing surface and the bottom load bearing surface is smaller at the rear surface than at the front surface. In such embodiments, the frame of the cervical column support device may be a hollow right isosceles trapezoidal prism-shaped frame, where the wide end, or base, of the right isosceles trapezoidal prism is the rear surface of the frame. In various examples according to one embodiment, the bottom and top load bearing surfaces are not coplanar, but rather lie in separate planes which intersect at a 2-10 (preferably 2-4) degree angle so as to provide the proper angle for the cervical vertebrae. These surfaces bear the weight and forces on the vertebrae and, according to one or more aspects, may be held in place primarily by frictional forces between the vertebrae and the serrated portions on the top and bottom load bearing surfaces.

According to at least one exemplary embodiment, the hollow prism-shaped frame may be constructed from at least one biocompatible material. In various examples of one embodiment, the biocompatible material may be a metal, a ceramic, a polymer, or a combination thereof.

The support may also include a plate attached to the front (anterior) portion and including screw holes allowing the plate to be connected to the vertebrae by screws. According to at least one embodiment, these screws do not provide primary support and are not load bearing. Their function, instead, is to hold the plate portion of the device in position. The support may be constructed of any bio-compatible material, such as titanium.

In some embodiments, the anterior plate is aligned along a plane (P) and the top and bottom load bearing surfaces between them form an axis of elongation (A) that is at a non-right angle relative to the plane (P).

These and other embodiments are pointed out with particularity in the claims annexed to and forming part of this disclosure. For a better understanding of the disclosed subject matter, its operating advantages and the specific objects attained by its uses, reference should be made to the accompanying drawings and descriptive matter which illustrate various examples of one embodiment.

BRIEF DESCRIPTION OF THE DRAWINGS

In order to better understand various examples of various embodiments, reference is made to the accompanying drawings, wherein:

FIG. 1 is a side view of one example anterior cervical column support device according to one embodiment.

FIG. 2 is a side view of one example anterior cervical column support device according to one embodiment, showing example details of the angles between the top load bearing surface and the bottom load bearing surface.

FIG. 3 is a top view of one example anterior cervical column support device according to one embodiment showing example serrations on the top load bearing surface of the support device.

FIG. 4 is an anterior or front view of the anterior cervical column support device showing the anterior plate and associated screw holes.

FIG. 5 is a detailed side view of one example top load bearing surface showing example serrations.

FIG. 9 is a cross sectional view of one example anterior cervical column support device according to one embodiment showing an example of how the side panels may connect to the frame.

FIG. 10 is a second cross sectional view of one example anterior cervical column support device according to one embodiment showing one example of a different method of connecting the side panels to the frame.

FIG. 11 is a cross sectional view of one example anterior cervical column support device according to one example embodiment showing a further example method of connecting the side panels to the frame.

FIG. 18 is a top view of a second alternative embodiment.

FIG. 19 is a cross sectional view of the embodiment of FIG. 18.

FIG. 20 is a cross sectional view of the embodiment of FIG. 18.

FIG. 21 is a side view of the embodiment of FIG. 18.

FIG. 22 is an end view of the embodiment of FIG. 18.

FIG. 23 is a cross sectional view of the embodiment of FIG. 18.

FIG. 24 is a top view of a third alternative embodiment.

FIG. 25 is a cross sectional view of the embodiment of FIG. 24.

FIG. 26 is a cross sectional view of the embodiment of FIG. 24.

FIG. 27 is a side view of the embodiment of FIG. 24.

FIG. 28 is an end view of the embodiment of FIG. 24.

FIG. 29 is a cross sectional view of the embodiment of FIG. 24.

FIG. 30 is a top view of a fourth alternative embodiment.

FIG. 31 is a cross sectional view of the embodiment of FIG. 30.

FIG. 32 is a cross sectional view of the embodiment of FIG. 30.

FIG. 33 is a side view of the embodiment of FIG. 30.

FIG. 34 is an end view of the embodiment of FIG. 30.

FIG. 35 is a cross sectional view of the embodiment of FIG. 30.

DETAILED DESCRIPTION OF THE EXEMPLARY EMBODIMENTS

Figure 8:
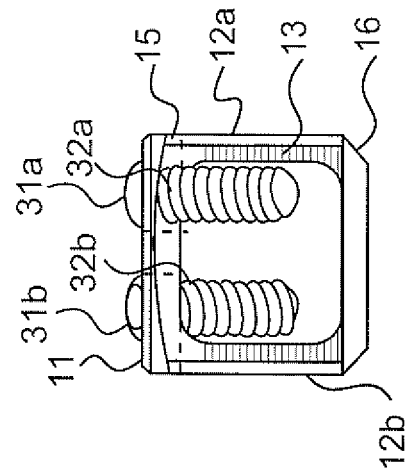
FIG. 8 is a top view of the FIG. 6 example anterior cervical column support device with the example associated screws.

For the purposes of this description, the term "opaque to X-rays" encompasses the ordinary and customary meaning of "X-ray opaque" as that phrase is known in the surgical implant arts at the time of this invention and includes, but is not limited to, an opacity to X-rays sufficient to be clearly visible in an X-ray photograph or X-ray digital image obtained using X-ray dose levels acceptable for X-ray imaging of a live subject and includes, but is not limited to, the X-ray opacity of human bone, the X-ray opacity of lead having a thickness of greater than approximately 1.5 mm, and opacity within the meaning of "practically opaque" by W. C. Roentgen.

For the purposes of this description, the term "transparent to X-rays" encompasses the ordinary and customary meaning of "X-ray transparent" as that phrase is known in the surgical implant arts at the time of this invention and includes, but is not limited to, the X-ray transmittance characteristic of human flesh (i.e., muscle tissue), and encompasses the transmittance described as "very transparent" by W. C. Roentgen such as, for example, that exhibited by very thin sheet of thin aluminum foil, and includes a characteristic such that an "X-ray transparent" structure is not clearly visible in an X-ray photograph or X-ray digital image obtained using X-ray dose levels acceptable for X-ray imaging of a live subject.

For the purposes of this description, the term "translucent to X-rays" encompasses the ordinary and customary meaning of "X-ray translucent" as that phrase is known in the surgical implant arts at the time of this invention and includes, but is not limited to, a characteristic such that an "X-ray translucent" structure may have a certain visibility in an X-ray photograph or X-ray digital image obtained using X-ray dose levels acceptable for X-ray imaging of a live subject, but does not fully obstruct visibility, in such an X-ray photograph or X-ray digital image, of other structures covered by the "X-ray translucent" structure from the perspective of the X-ray energy source.

The term "at least X-ray translucent" means an X-ray transmittance at least equal to "X-ray translucent" includes, but is not limited to, "transparent to X-rays."

Referring now to the drawings, in which like numerals refer to like components or steps, there are disclosed various, example aspects of various examples of one or more embodiments. Referring now to FIG. 1 this figure is a side view showing an exemplary embodiment of an anterior cervical column support device.

With continuing reference to FIG. 1, in various examples of one embodiment, an anterior cervical column support device 10 according to the present application may be constructed as a hollow prism-shaped frame, preferably a hollow right prism-shaped frame, comprising an anterior plate 11, two side surfaces 12a and 12b, a rectangular shaped top load bearing surface 13, a rectangular shaped bottom load bearing surface 14, a front or anterior surface 15 and a rear or posterior surface 16. At least a portion of front surface 15 and at least a portion of rear surface 16 are opaque to X-rays. In the depicted example, the anterior plate 11 is attached to the front surface 15 of the support device 10. The example anterior plate 11 also includes two screw holes for attaching the plate portion to two adjacent vertebral bodies. As can be seen, the two side surfaces 12a and 12b are not skeletal in configuration. Instead, side surfaces 12a and 12b extend between, and preferably are attached between the front surface and the rear surface, with each side surface comprising a solid side panel 25 which is transparent or translucent to X-rays. Side surfaces 12a and 12b may also extend between, and may be attached between, the front surface and the rear surface. Front surface 15 and anterior plate 11 together have a thickness defined as the difference between length L2 and length L1, where L1 and L2 are defined in FIG. 3.

Still referring to FIG. 1, in various examples of one embodiment, the anterior cervical column support device 10 may be constructed as a hollow isosceles trapezoidal shaped prism-shaped frame, preferably a hollow isosceles trapezoidal shaped right prism-shaped frame. Referring now to FIG. 3, in a right prism-shaped frame, the width "W" of the front or anterior surface 15 and the rear surface 16 may be equal. Other embodiments include prism-shaped frames which are not right prisms, and therefore allow differences between the width "W" of the anterior surface 15 and the rear surface 16 to match individual anatomic variations. Referring to the side-view depicted at FIG. 2, in exemplary embodiments in which the anterior cervical column support device 10 is constructed as an isosceles trapezoidal-shaped frame, the height "A" of the rear surface 16 is shorter than the height "B" of the front surface 15. This configuration forms the isosceles trapezoidal shape. The top load bearing surface 13 and the bottom load bearing surface 14 are skeletal in configuration. Referring again to the top view depicted at FIG. 3, each of these surfaces provides access to the interior 17 of the support device 10.

In various examples of one embodiment, the anterior cervical column support device 10 is constructed as a hollow prism-shaped frame. In such a frame, the width of the front or anterior surface 15 and the rear surface 16 may be unequal. In various examples of one embodiment, the width of the front surface 15 is greater than the width of the rear surface 16. In various examples of one embodiment, the width of the front surface 15 is less than the width of the rear surface 16. The height "A" of the rear surface 16 may be less than or equal to the height "B" of the front surface 15, as seen in the side view of FIG. 2. Again, the top load bearing surface 13 and the bottom load bearing surface 14 are skeletal in configuration.

The interior 17 of the support device 10 receives bone grafting material. This bone grafting material allows the vertebrae on each side of the support device 10 to fuse together. Useful hone grafting materials include, as illustrative examples, cartilage; bone from autologous or allograft sources; demineralized bone matrix; bone morphogenic proteins in conjunction with a carrier, such as collagen; hydroxylapatite, calcium phosphates, or other ceramic materials, alone or in combination with bone marrow aspirate; and mixtures thereof.

As shown in FIG. 1, a side view of the anterior cervical column support device 10 shows the front plate 11 attached to the anterior surface 15 of the support device 10. It also shows a side surface 12a. In the depicted example, each side surface 12a and 12b has the same shape and size. FIG. 1 also shows a side view of the top load bearing surface 13 and the bottom load bearing surface 14. These surfaces 13 and 14 may have the same size and shape and, therefore are named differently for the purpose of description only. Each surface 13 and 14 may be formed as a high friction surface by including serrations 18.

In various examples of one embodiment, each surface 13 and 14 may be formed as a high friction surface without serrations by, for example roughening the top and bottom load bearing surfaces. Roughening the top and bottom load bearing surfaces may be done by, for example, etching the top and bottom load bearing surfaces or sandblasting the top and bottom load bearing surfaces to provide a 3D surface texture. Photoetching may be used to provide the surface with a defined 3D pattern having a depth of from 0.013 to 2.00 mm, preferably 0.02 to 0.05 mm, to support bone ingrowth.

FIG. 2 shows a detailed side view of the example anterior cervical column support device 10. It shows the height "B" of the front surface 15 and the height "A" of the rear surface 16. The side surfaces 12a and 12b have a trapezoidal shape which can clearly be seen from FIG. 2. The front end of the trapezoid has a height "B" and the rear end of the trapezoid has a height "A." Height "A" and height "B" are designed for specific areas within the cervical region of the spine and specifically are designed to fit between certain vertebrae in that area. The heights "A" and "B" provide the proper spacing between the vertebra while the difference between the heights "A" and "B" create an angle a1 between the anterior surface 15 and the top load bearing surface 13 and an angle a2 between the rear surface 16 and the top load bearing surface 13. Angle a1 may, for example, be between 85 and 89 degrees whereas the corresponding angle a2 may be is between, for example, 91 and 95 degrees. In various examples of one embodiment, angle a1 may be between, for example, 88 and 89 degrees whereas angle a2 may be between for example 91 and 92 degrees. Angles a1 and a2 are also present with respect to the bottom load bearing surface 14 as it is attached to the front or anterior surface 15 and the rear surface 16. The angles a1 and a2, the top load bearing surface 13 and the bottom load bearing surface 14 form a trapezoidal shape which holds the vertebrae in the proper position. In this manner, the support device 10 holds the proper lordodic balance and restores the sagittal balance between the vertebrae in the cervical area of the spine.

FIG. 3 shows a top view of the anterior cervical support device 10. In the depicted example, the width "W" of the top load bearing surface 13, the bottom load bearing surface 14, the front surface 15 and the rear surface 16 are all equal. In a preferred embodiment, the width may be, for example, 12 to 15 millimeters. However, this width can vary according to the size of the vertebrae of the cervical area of the spine of the particular patient. In the FIG. 3 depiction, the serrations 18 on the top load bearing surface 13 are visible as is the rectangular shape of the top load bearing surface 13.

A detailed view of one example implementation of these serrations 18 is shown in FIG. 5. Arrow 21 in FIG. 5 indicates the direction of insertion of the support device 10, where the rear surface of the support device is inserted first. With respect to the direction of insertion, the example serrations 18 include a sloping rear side 19 and a perpendicular front side 20. This allows for easy movement in one direction and difficult movement in the other direction. These serrations 18 provide the primary frictional support for the support device 10.

FIG. 4 shows a detailed view of the front plate 11, while FIG. 1 includes a cross sectional view of front plate 11. The front plate 11 is attached to the front surface 15 of the anterior cervical column support device 10. The front plate 11 includes two clearance holes 22a and 22b, as seen in FIGS. 1 and 4. The clearance holes 22a and 22b are designed to receive a plurality of medical fasteners, and are preferably angled away from each other, so as to allow the user to direct a first medical fastener, which may be a screw or a bone anchor, through hole 22*a* into the vertebra supported by top load bearing surface 13; and to drive a second medical fastener, which may be a screw or a bone anchor, through hole 22*b* into the vertebra supported by bottom load bearing surface 14 (Note: Vertebrae are not shown in FIGS. 1 and 4). The clearance holes 22*a* and 22*b* are depicted as indented and offset screw holes 22*a* and 22*b*. Screw holes 22*a* and 22*b* may include indentations 23*a* and 23*b*, adapted to receive a head of a screw.

In certain embodiments, each solid side panel may be between, for example, 0.1 mm thick and 0.3 mm thick and, as such, serves to increase the strength of the cervical column support device while providing X-ray transparency. A cervical column support device according to various embodiments described in the present disclosure may be compared to a comparative skeletal cervical column support device of identical external shape and size. First, a cervical column support device according to embodiments described in the present disclosure differs from the comparative skeletal device in that its side surfaces include solid side panels that are at least X-ray translucent while, in contrast, the side surfaces of the comparative skeletal device include openings through which X-rays may pass. If the openings in the comparative skeletal device are the same size as the side panels in the device according to the disclosed, the side panels act of the example according to the present embodiments increase the strength of the present cervical column support device by a factor of between two and 10, when compared to the strength of the comparative skeletal device lacking such side panels. As readily understood by a person of ordinary skills in the art upon reading this disclosure, the precise amount by which the side panels will increase the strength of the device is dependent on a number of factors, including the material forming the side panels and thickness of the side panels. Assuming a titanium frame with X-ray transparent or X-ray translucent titanium foil side panels having a thickness of 0.2 to 0.3 mm, the side panels typically act to increase the strength of the cervical column support device disclosed herein by a factor of at least two.

In other words, the anterior cervical column support device has solid side panels that are constructed and arranged so that a first anterior cervical column support device with the solid side panels has a first strength; and a second, comparative, anterior cervical column support device formed by a skeletal frame without side panels has a second strength. The first strength is from two to ten times greater than the second strength. Given that the only structural differences between the first anterior cervical column support device and the second, comparative, anterior cervical column lies in the presence of side panels on the first support device but not the second device, the side panels therefore function as load bearing members which increase the strength of the anterior cervical column support device.

Alternatively, if improved visibility of the interior of a cervical column support device is desired, the side panels of the present cervical column support device may be made larger than the openings in the side panels of the comparative cervical column support device, without making the present device weaker than the comparative device. This may be accomplished because the solid side panels in the present cervical column support device add strength to the device. The larger X-ray-transparent side panels thus allow increased visibility while maintaining strength.

Figure 7:
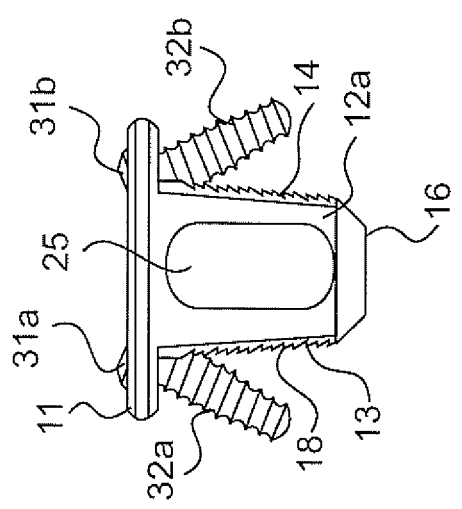
FIG. 7 is a side view of the FIG. 6 example anterior cervical column support device with the example associated screws.
Figure 6:
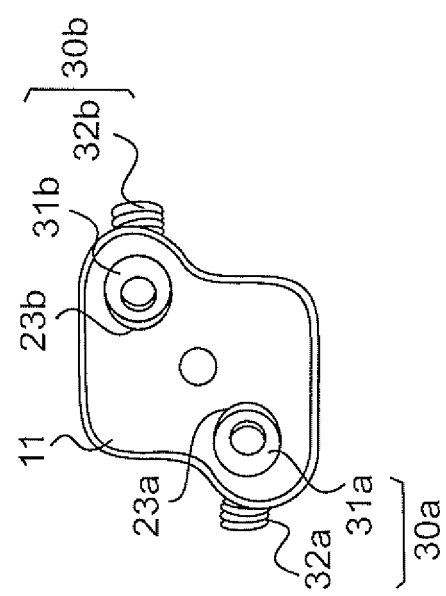
FIG. 6 is an anterior or front view of one example anterior cervical column support device according to one embodiment showing an anterior plate with an example of associated screws.
Figure 14:
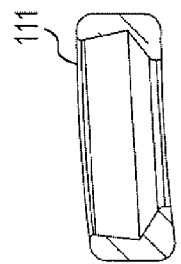
FIG. 14 is a cross sectional view of the embodiment of FIG. 12.
Figure 17:
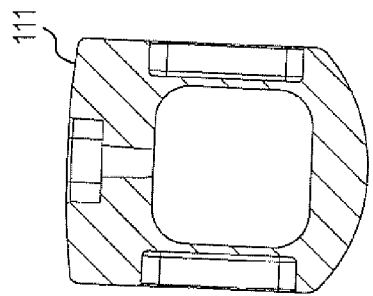
FIG. 17 is a cross sectional view of the embodiment of FIG. 12.
Figure 13:
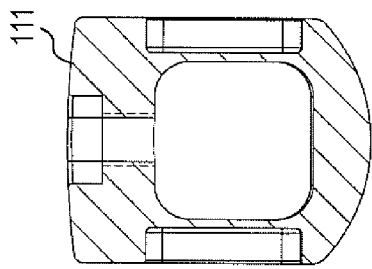
FIG. 13 is a cross sectional view of the embodiment of FIG. 12.
Figure 16:
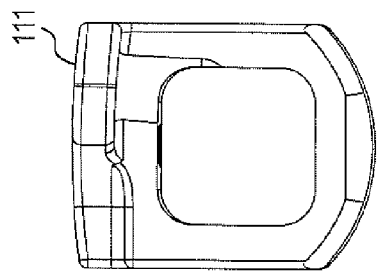
FIG. 16 is an end view of the embodiment of FIG. 12.
Figure 12:
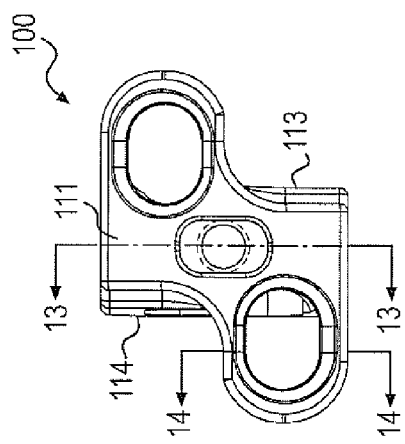
FIG. 12 is a top view of a first alternative embodiment.
Figure 15:
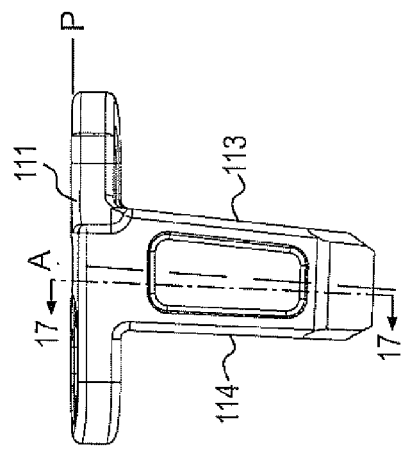
FIG. 15 is a side view of the embodiment of FIG. 12.

FIGS. 6-8 illustrate one example positioning of screws 30*a* and 30*b* in an example cervical column support device according to one example embodiments herein. Each example screw 30*a* and 30*b* includes a head (31*a* and 31*b*, respectively) and a threaded shaft (32*a* and 32*b*, respectively). Screw 30*a* passes through screw hole 22*a* in front plate 11, while screw head 31*a* fits into indentation 23*a*. Threaded shaft 32*a* screws into a cervical vertebra positioned on top load bearing surface 13. Screw 30*b* passes through screw hole 22*b* in front plate 11, while screw head 31*b* fits into indentation 23*b*. Threaded shaft 32*b* screws into a second cervical vertebra, where the bottom load bearing surface 14 is supported by the upper surface of the second cervical vertebra.

The screws can be made of any bio-compatible material. In various examples of one embodiment, the screws may be made of a bio-compatible material selected from the group consisting of titanium, nickel, aluminum, nickel-titanium alloys, titanium-aluminum alloys, titanium-aluminum-vanadium alloys, and mixtures thereof. The specific material for, and length of the screws are readily identified by a person of ordinary skill in the art upon reading this disclosure. For illustrative example, in various examples of one embodiment, the screws may be titanium uni-cortical screws having a length of, for example, 14 millimeter.

In various examples of one embodiment, all components of the anterior cervical column support device may be made of at least one biocompatible material. The at least one biocompatible material may be selected from the group consisting of:

metals selected from the group consisting of titanium, nickel, aluminum, nickel-titanium alloys, titanium-aluminum alloys, titanium-aluminum-vanadium alloys, and mixtures thereof;

polymers selected from the group consisting of polyethylene, polypropylene, polysulfone, and polyetheretherketone (PEEK); and ceramics selected from the group consisting of alumina, zirconia, calcium oxides, calcium phosphates, and hydroxyapatite. Tricalcium phosphate and hydroxyapatite are of particular interest among ceramics, as they have been used as artificial bone.

An anterior cervical column support device according to one or more of the embodiments, including the specific examples described herein, may also be formed in whole or in part from natural bone tissue. For example, an anterior cervical column support device according to various example embodiments may be engineered or shaped into the desired right prismatic structure from bone tissue harvested from an autologous source; i.e., the patient's own bone tissue. Alternatively, an anterior cervical column support device according to one or more may be formed from allograft bone tissue from a human donor or xenograft bone tissue from a nonhuman donor, such as a pig, cow, or baboon.

According to one aspect of one or more various examples of one embodiment, the anterior cervical column support device may be the device manufactured from a biocompatible metal or metal alloy selected from the group consisting of titanium, nickel-titanium alloys, titanium-aluminum alloys, titanium-aluminum-vanadium alloys, and mixtures thereof. According to one aspect, an anterior cervical column support device having one or more of the embodiments may be manufactured from a single biocompatible metal or metal alloy selected from the group consisting of titanium, nickel-titanium alloys, titanium-aluminum alloys, and titanium-aluminum-vanadium alloys. In Various examples of one embodiment, the anterior cervical column support device is manufactured from a titanium-aluminum-vanadium alloy, such as a titanium-based 6AL-4V ELI alloy.

In one or more examples of an anterior cervical column support device according to various embodiments, the device may be made of a metal such as titanium, nickel, aluminum, or an alloy thereof, the metal may be coated with a protective ceramic coating. According to one aspect, an aluminum cervical column support device may be anodized. Anodizing grows a layer of aluminum oxide on the metal surface by passing a direct current through an electrolytic solution, with the aluminum object serving as the anode. The current releases hydrogen at the cathode and oxygen at the surface of the aluminum anode, creating a build-up of aluminum oxide. This oxide surface is very hard. While most aluminum averages about 35 to 40 on the Rockwell C scale, the oxide layer averages 52 to 55. A cervical column support device made of titanium may be anodized in a similar fashion. Protective ceramic coatings may also be produced by thermal oxidation of the metal cervical column support device. For example, heat treating a titanium or titanium alloy support device according to the various example embodiments, to several hundred degrees Celsius in an oxygen-containing atmosphere produces a micrometer-thick TiO2 surface layer.

Surface coatings on metal cervical column support devices also may be used to aid the process of osteointegration between the human cervical bone and the metal implants. As an example, hydroxyapatite or tricalcium phosphate may be deposited on anodized titanium to aid in osteointegration of bone tissue into the surface layer of surface layer of the metal implant. Etching or sandblasting of the metal surface may also aid in osteointegration by providing the metal implant with a roughened surface layer having nooks and crannies into which bone tissue may grow. Etching or sandblasting may be applied to all surfaces of the cervical column support devices; or etching or sandblasting may be restricted to the top and bottom load bearing surfaces 13 and 14.

In various examples of one embodiment of the anterior cervical column support device, wherein the top load bearing surface 13, the bottom load bearing surface 14, the rear surface 16, and the front surface 15 are constructed from a first biocompatible material; and the solid side panels 25 are constructed from a second biocompatible material. In various examples of one embodiment, the first bio-compatible material may be a metal or metal alloy, a ceramic, or a polymer; and the second bio-compatible material is different from the first bio-compatible material, and may be a metal or metal alloy, a ceramic, or a polymer.

In various examples of one embodiment, the first biocompatible material may be titanium, nickel, aluminum, nickel-titanium alloys, titanium-aluminum alloys, titanium-aluminum-vanadium alloys, or a mixture thereof. The second bio-compatible material may be a ceramic such as alumina, zirconia, calcium oxides, calcium phosphates, or hydroxyapatite; a polymer such as polyethylene, polypropylene, polycarbonate, polyimide, polysulfone, or polyetheretherketone (PEEK); or an X-ray transparent metal film, such as a titanium foil or an aluminum foil.

In various examples of one embodiment, the top load bearing surface 13, the bottom load bearing surface 14, the rear surface 16, and the front surface 15 may be constructed from natural bone tissue or artificial bone as a first, X-ray opaque, bio-compatible material; and the solid side panels are constructed from an X-ray transparent metal film, such as a titanium foil or an aluminum foil.

As seen in the cross sectional view of FIG. 9, each solid side panel 25 which is at least X-ray translucent may be formed as an integral part of the hollow prism-shaped frame. The solid side panels 25 and the remainder of the frame may be manufactured as a single element. The solid side panels 25 are at least X-ray translucent and have an X-ray transmittance substantially less than the remainder of the frame because the side panels are thinner than the remainder of the frame. For example, the anterior cervical column support device may be manufactured from titanium, nickel, aluminum, nickel-titanium alloys, titanium-aluminum alloys, titanium-aluminum-vanadium alloys, or a mixture thereof. The top and bottom load bearing surfaces and the front and rear surfaces may be constructed from metal that which is, for example, approximately 2 to 5 millimeters thick. These metal surfaces are comparatively thick, and therefore are substantially opaque to X-rays. The side panels 25 may be constructed from a metal which is, for example, approximately 0.1 to 0.3 millimeters thick. The side panels 25 therefore comprise comparatively thin metal surfaces which are at least X-ray translucent.

As seen in the cross sectional view of FIG. 10, each solid side panel 25 which is at least X-ray translucent may be formed as a separate part of the cervical column support device from the hollow prism-shaped frame. The solid side panels 25a may each be formed as a sheet or foil, and the remainder of the frame may be manufactured as a single element having openings 25c in side surfaces 12a and 12b. The solid side panels 25a may then be secured to the remainder of the frame so as to cover openings 25c. The solid side panels 25a may be secured over openings 25c by means of an adhesive. Alternatively, if solid side panels 25a and the frame are made of metal, solid side panels 25a may be secured over openings 25c by means of welding or brazing.

In various examples of one embodiment, solid side panels 25a and the frame are made of the same material. In such embodiments, the solid side panels 25a are manufactured as thin metal foils, while the remainder of the frame is manufactured from substantially thicker metal. For example, the top and bottom load bearing surfaces and the front and rear surfaces of the anterior cervical column support device may be manufactured from metal which is approximately 2 to 5 millimeters thick. These metal surfaces are comparatively thick, and therefore are substantially opaque to X-rays. The side panels 25a are constructed from metal foils which are approximately 0.1 to 0.3 millimeters thick, and are therefore at least X-ray translucent. When solid side panels 25a are bonded to the frame, the resulting anterior cervical column support device has an X-ray opaque frame with side panels 25a that are at least X-ray translucent.

In various examples of one embodiment, solid side panels 25a and the frame are made of materials having different X-ray transparencies. For example, the solid side panels 25a may be manufactured from as a plate or foil which is 0.1-5 mm thick of a material which is transparent to X-rays, such as an X-ray transparent polymer or ceramic sheet; while the frame may be manufactured from X-ray opaque metal which is approximately 2 to 5 millimeters thick. When solid side panels 25a are bonded to the frame, the resulting anterior cervical column support device has an X-ray opaque frame with side panels 25a that are at least X-ray translucent.

Referring now to the drawings, in which like numerals refer to like components or steps, there are disclosed various, example aspects of various examples of one or more embodiments. Referring now to FIG. 1 this figure is a side view showing an exemplary embodiment of an anterior cervical column support device.

With continuing reference to FIG. 1, in various examples of one embodiment, an anterior cervical column support device 10 according to the present application may be constructed as a hollow prism-shaped frame, preferably a hollow right prism-shaped frame, comprising an anterior plate 11, two side surfaces 12a and 12b, a rectangular shaped top load bearing surface 13, a rectangular shaped bottom load bearing surface 14, a front or anterior surface 15 and a rear or posterior surface 16. At least a portion of front surface 15 and at least a portion of rear surface 16 are opaque to X-rays. In the depicted example, the anterior plate 11 is attached to the front surface 15 of the support device 10. The example anterior plate 11 also includes two screw holes for attaching the plate portion to two adjacent vertebral bodies. As can be seen, the two side surfaces 12a and 12b are not skeletal in configuration. Instead, side surfaces 12a and 12b extend between, and preferably are attached between the front surface and the rear surface, with each side surface comprising a solid side panel 25 which is transparent or translucent to X-rays. Side surfaces 12a and 12b may also extend between, and may be attached between, the front surface and the rear surface. Front surface 15 and anterior plate 11 together have a thickness defined as the difference between length L2 and length L1, where L1 and L2 are defined in FIG. 3.

Still referring to FIG. 1, in various examples of one embodiment, the anterior cervical column support device 10 may be constructed as a hollow isosceles trapezoidal shaped prism-shaped frame, preferably a hollow isosceles trapezoidal shaped right prism-shaped frame. Referring now to FIG. 3, in a right prism-shaped frame, the width "W" of the front or anterior surface 15 and the rear surface 16 may be equal. Other embodiments include prism-shaped frames which are not right prisms, and therefore allow differences between the width "W" of the anterior surface 15 and the rear surface 16 to match individual anatomic variations. Referring to the side-view depicted at FIG. 2, in exemplary embodiments in which the anterior cervical column support device 10 is constructed as an isosceles trapezoidal-shaped frame, the height "A" of the rear surface 16 is shorter than the height "B" of the front surface 15. This configuration forms the isosceles trapezoidal shape. The top load bearing surface 13 and the bottom load bearing surface 14 are skeletal in configuration. Referring again to the top view depicted at FIG. 3, each of these surfaces provides access to the interior 17 of the support device 10.

In various examples of one embodiment, the anterior cervical column support device 10 is constructed as a hollow prism-shaped frame. In such a frame, the width of the front or anterior surface 15 and the rear surface 16 may be unequal. In various examples of one embodiment, the width of the front surface 15 is greater than the width of the rear surface 16. In various examples of one embodiment, the width of the front surface 15 is less than the width of the rear surface 16. The height "A" of the rear surface 16 may be less than or equal to the height "B" of the front surface 15, as seen in the side view of FIG. 2. Again, the top load bearing surface 13 and the bottom load bearing surface 14 are skeletal in configuration.

The interior 17 of the support device 10 receives bone grafting material. This bone grafting material allows the vertebrae on each side of the support device 10 to fuse together. Useful bone grafting materials include, as illustrative examples, cartilage; bone from autologous or allograft sources; demineralized bone matrix; bone morphogenic proteins in conjunction with a carrier, such as collagen; hydroxylapatite, calcium phosphates, or other ceramic materials, alone or in combination with bone marrow aspirate; and mixtures thereof.

As shown in FIG. 1, a side view of the anterior cervical column support device 10 shows the front plate 11 attached to the anterior surface 15 of the support device 10. It also shows a side surface 12a. In the depicted example, each side surface 12a and 12b has the same shape and size. FIG. 1 also shows a side view of the top load bearing surface 13 and the bottom load bearing surface 14. These surfaces 13 and 14 may have the same size and shape and, therefore are named differently for the purpose of description only. Each surface 13 and 14 may be formed as a high friction surface by including serrations 18.

In various examples of one embodiment, each surface 13 and 14 may be formed as a high friction surface without serrations by, for example roughening the top and bottom load bearing surfaces. Roughening the top and bottom load bearing surfaces may be done by, for example, etching the top and bottom load bearing surfaces or sandblasting the top and bottom load bearing surfaces to provide a 3D surface texture. Photoetching may be used to provide the surface with a defined 3D pattern having a depth of from 0.013 to 2.00 mm, preferably 0.02 to 0.05 mm, to support bone ingrowth.

FIG. 2 shows a detailed side view of the example anterior cervical column support device 10. It shows the height "B" of the front surface 15 and the height "A" of the rear surface 16. The side surfaces 12a and 12b have a trapezoidal shape which can clearly be seen from FIG. 2. The front end of the trapezoid has a height "B" and the rear end of the trapezoid has a height "A." Height "A" and height "B" are designed for specific areas within the cervical region of the spine and specifically are designed to fit between certain vertebrae in that area. The heights "A" and "B" provide the proper spacing between the vertebra while the difference between the heights "A" and "B" create an angle a1 between the anterior surface 15 and the top load bearing surface 13 and an angle a2 between the rear surface 16 and the top load bearing surface 13. Angle a1 may, for example, be between 85 and 89 degrees whereas the corresponding angle a2 may be is between, for example, 91 and 95 degrees. In various examples of one embodiment, angle a1 may be between, for example, 88 and 89 degrees whereas angle a2 may be between for example 91 and 92 degrees. Angles a1 and a2 are also present with respect to the bottom load bearing surface 14 as it is attached to the front or anterior surface 15 and the rear surface 16. The angles a1 and a2, the top load bearing surface 13 and the bottom load bearing surface 14 form a trapezoidal shape which holds the vertebrae in the proper position. In this manner, the support device 10 holds the proper lordodic balance and restores the sagittal balance between the vertebrae in the cervical area of the spine.

FIG. 3 shows a top view of the anterior cervical support device 10. In the depicted example, the width "W" of the top load bearing surface 13, the bottom load bearing surface 14, the front surface 15 and the rear surface 16 are all equal. In a preferred embodiment, the width may be, for example, 12 to 15 millimeters. However, this width can vary according to the size of the vertebrae of the cervical area of the spine of the particular patient. In the FIG. 3 depiction, the serrations 18 on the top load bearing surface 13 are visible as is the rectangular shape of the top load bearing surface 13.

A detailed view of one example implementation of these serrations 18 is shown in FIG. 5. Arrow 21 in FIG. 5 indicates the direction of insertion of the support device 10, where the rear surface of the support device is inserted first. With respect to the direction of insertion, the example serrations 18 include a sloping rear side 19 and a perpendicular front side 20. This allows for easy movement in one direction and difficult movement in the other direction. These serrations 18 provide the primary frictional support for the support device 10.

FIG. 4 shows a detailed view of the front plate 11, while FIG. 1 includes a cross sectional view of front plate 11. The front plate 11 is attached to the front surface 15 of the anterior cervical column support device 10. The front plate 11 includes two clearance holes 22a and 22b, as seen in FIGS. 1 and 4. The clearance holes 22a and 22b are designed to receive a plurality of medical fasteners, and are preferably angled away from each other, so as to allow the user to direct a first medical fastener, which may be a screw or a bone anchor, through hole 22*a* into the vertebra supported by top load bearing surface 13; and to drive a second medical fastener, which may be a screw or a bone anchor, through hole 22*b* into the vertebra supported by bottom load bearing surface 14 (Note: Vertebrae are not shown in FIGS. 1 and 4). The clearance holes 22*a* and 22*b* are depicted as indented and offset screw holes 22*a* and 22*b*. Screw holes 22*a* and 22*b* may include indentations 23*a* and 23*b*, adapted to receive a head of a screw.

In certain embodiments, each solid side panel may be between, for example, 0.1 mm thick and 0.3 mm thick and, as such, serves to increase the strength of the cervical column support device while providing X-ray transparency. A cervical column support device according to various embodiments described in the present disclosure may be compared to a comparative skeletal cervical column support device of identical external shape and size. First, a cervical column support device according to embodiments described in the present disclosure differs from the comparative skeletal device in that its side surfaces include solid side panels that are at least X-ray translucent while, in contrast, the side surfaces of the comparative skeletal device include openings through which X-rays may pass. If the openings in the comparative skeletal device are the same size as the side panels in the device according to the disclosed, the side panels act of the example according to the present embodiments increase the strength of the present cervical column support device by a factor of between two and 10, when compared to the strength of the comparative skeletal device lacking such side panels. As readily understood by a person of ordinary skills in the art upon reading this disclosure, the precise amount by which the side panels will increase the strength of the device is dependent on a number of factors, including the material forming the side panels and thickness of the side panels. Assuming a titanium frame with X-ray transparent or X-ray translucent titanium foil side panels having a thickness of 0.2 to 0.3 mm, the side panels typically act to increase the strength of the cervical column support device disclosed herein by a factor of at least two.

In other words, the anterior cervical column support device has solid side panels that are constructed and arranged so that a first anterior cervical column support device with the solid side panels has a first strength; and a second, comparative, anterior cervical column support device formed by a skeletal frame without side panels has a second strength. The first strength is from two to ten times greater than the second strength. Given that the only structural differences between the first anterior cervical column support device and the second, comparative, anterior cervical column lies in the presence of side panels on the first support device but not the second device, the side panels therefore function as load bearing members which increase the strength of the anterior cervical column support device.

Alternatively, if improved visibility of the interior of a cervical column support device is desired, the side panels of the present cervical column support device may be made larger than the openings in the side panels of the comparative cervical column support device, without making the present device weaker than the comparative device. This may be accomplished because the solid side panels in the present cervical column support device add strength to the device. The larger X-ray-transparent side panels thus allow increased visibility while maintaining strength.

In certain embodiments such as the example shown in FIG. 11, guides 26 may be positioned on the inner surface of side surfaces 12*a* and 12*b* of the frame. Alternatively, guides 26 may be positioned on the outer surface of side surfaces 12*a* and 12*b* of the frame. Solid side panels 25*b* may then be positioned on the frame by sliding the edges of side panels 25*b* into guides 26.

FIGS. 12-17 illustrate a first alternative embodiment of a spacer 100. In this embodiment the anterior plate 111 has a top surface generally arranged on a plane (P), and top and bottom load bearing surfaces 113 and 114 have between them an included angle centered along an axis (A). In this embodiment, the axis (A) is arranged at a non-right angle of 86 degrees relative to the plane (P) of the top surface of the anterior plate 111. This angle allows the support device to accommodate an included angle between the first and second spinal vertebrate. Also, while the description describes a top load surface 113 and a bottom load surface 114, the device may be installed "upside down" that is with the surface 114 being on top and the surface 113 being on bottom. Other than as described above, the insert may have any of the features that were described with respect to the embodiment of FIGS. 1-11. In particular, this embodiment may include side surfaces each comprising a solid panel which is X-ray translucent, although the side panel is not shown in the drawing figures for this embodiment. Although the top surface or anterior plate 111 is substantially planar in the view of FIG. 15, it will be appreciated from FIGS. 13, 16 and 17 that it may have some degree of a crown or curvature when viewed from that angle.

FIGS. 18-23 illustrate a second alternative embodiment of a spacer 200. In this embodiment the anterior plate 211 has a top surface generally arranged on a plane (P), and top and bottom load bearing surfaces 213 and 214 have between them an included angle centered along an axis (A). In this embodiment, the axis (A) is arranged at a non-right angle of 86 degrees relative to the plane (P) of the top surface of the anterior plate 211. This angle allows the support device to accommodate an included angle between the first and second spinal vertebrate. Also, while the description describes a top load surface 213 and a bottom load surface 214, the device may be installed "upside down" that is with the surface 214 being on top and the surface 213 being on bottom. Other than as described above, the insert may have any of the features that were described with respect to the embodiment of FIGS. 1-11. In particular, this embodiment may include side surfaces each comprising a solid panel which is X-ray translucent, although the side panel is not shown in the drawing figures for this embodiment. Although the top surface of anterior plate 211 is substantially planar in the view of FIG. 15, it will be appreciated from FIGS. 19, 22 and 23 that it may have some degree of a crown or curvature when viewed from that angle.

FIGS. 24-29 illustrate a third alternative embodiment. In this embodiment the anterior plate 311 has a top surface generally arranged on a plane (P), and top and bottom load bearing surfaces 313 and 314 have between them an included angle centered along an axis (A). In this embodiment, the axis (A) is arranged at a non-right angle of 82 degrees relative to the plane (P) of the top surface of the anterior plate 311. This angle allows the support device to accommodate an included angle between the first and second spinal vertebrate. Also, while the description describes a top load surface 313 and a bottom load surface 314, the device may be installed "upside down" that is with the surface 314 being on top and the surface 313 being on bottom. Other than as described above, the insert may have any of the features that were described with respect to the embodiment of FIGS. 1-11. In particular, this embodiment may include side surfaces each comprising a solid panel which is X-ray translucent, although the side panel is not shown in the drawing figures for this embodiment. Although the top surface of the anterior place 311 is substantially planar in the view of FIG. 15, it would be appreciated from FIGS. 25, 28 and 29 that it may have some degree of a crown or curvature when viewed from that angle.

FIGS. 30-35 illustrate a fourth alternative embodiment. In this embodiment the anterior plate 411 has a top surface generally arranged on a plane (P), and top and bottom load bearing surfaces 413 and 414 have between them an included angle centered along an axis (A). In this embodiment, the axis (A) is arranged at a non-right angle of 82 degrees relative to the plane (P) of the top surface of the anterior plate 411. This angle allows the support device to accommodate an included angle between the first and second spinal vertebrate. Also, while the description describes a top load surface 413 and a bottom load surface 414, the device may be installed "upside down" that is with the surface 414 being on top and the surface 413 being on bottom. Other than as described above, the insert may have any of the features that were described with respect to the embodiment of FIGS. 1-11. In particular, this embodiment may include side surfaces each comprising a solid panel which is X-ray translucent, although the side panel is not shown in the drawing figures for this embodiment. Although the top surface of the anterior plate 411 is substantially planar in the view of FIG. 15, it would be appreciated from FIGS. 31, 34 and 35 that it may have some degree of a crown or curvature when viewed from that angle.

Figure 36:
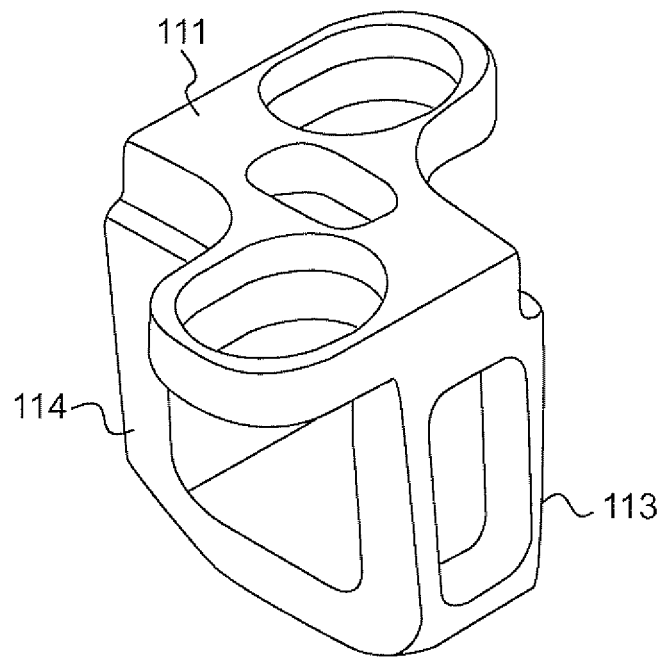
FIG. 36 is a perspective view of the embodiment of FIG. 12.

FIG. 36 is a perspective view of the third alternative embodiment described above.

Figure 37:
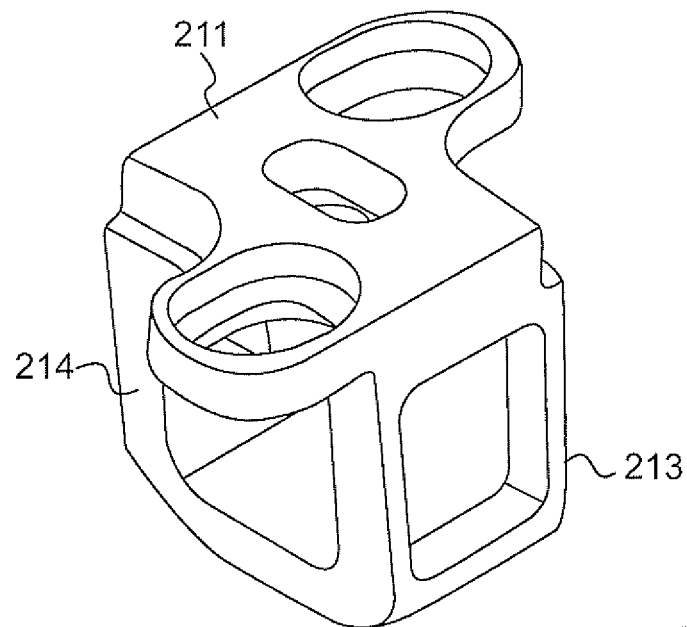
FIG. 37 is a perspective view of the embodiment of FIG. 18.

FIG. 37 is a perspective view of the second alternative embodiment described above.

Figure 39:
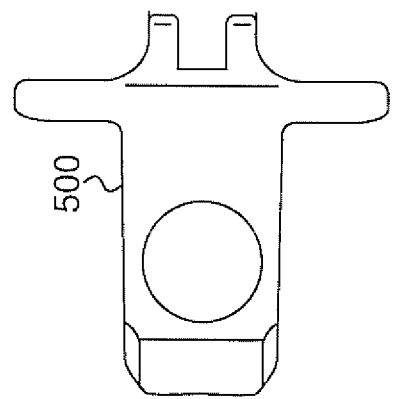
FIG. 39 is a side view of a spacer element.
Figure 38:
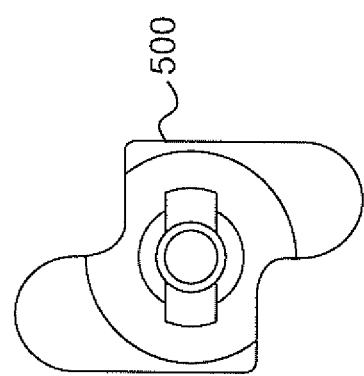
FIG. 38 is a top view of a spacer element.
Figure 40:
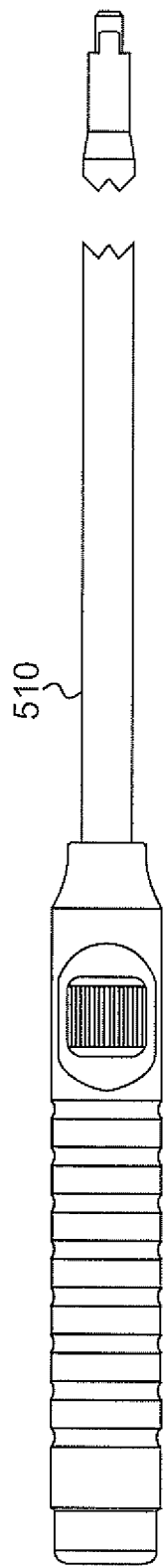
FIG. 40 is a side view of a spacer element insertion tool.
Figure 41:
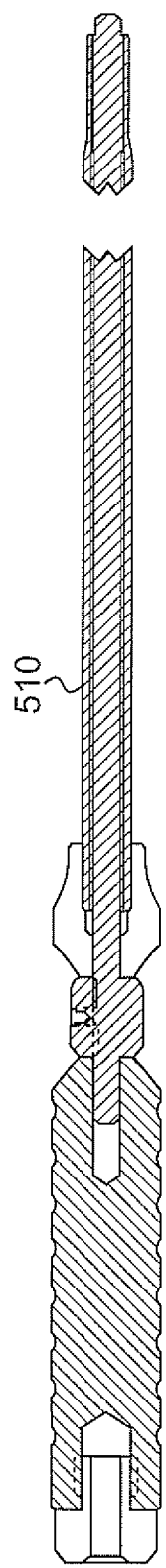
FIG. 41 is a cross sectional view of the tool of FIG. 40.

FIGS. 38 and 39 illustrate a spacer 500 that can be used to size the graft site on the vertebra body with the outline support device on top. This allows the surgeon to test the proper height of the graft site on top of the support device providing a confirmation of what area of the vertebral body may need to be adjusted so that the support device will rest flush on the vertebra body. With the spacer in the vertebral disk space, the surgeon can take a lateral X-ray to confirm which column support device would be most desirable for final placement, such as the right degree angle embodiment disclosed in FIGS. 1-11, one of the 86 degree embodiments described above, or one of the 82 degree angle embodiments described above. A jig can be provided to lay over the lateral X-ray in surgery to confirm with degree of column support will provide optimum fit. FIGS. 40 and 41 describe a handle 510 that can be used to insert the sizing spacer.

It will be apparent to those skilled in the art that various modifications and variations can be made to the anterior cervical spinal column support device as disclosed herein. Thus, it is intended that the present invention encompasses such modifications and variations, provided they come within the scope of the appended claims and their equivalents.

Although the various examples of one embodiment have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. An inter-vertebral implant for insertion between a first spinal vertebra and a second spinal vertebra, comprising:
    a hollow frame top load bearing surface and a bottom load bearing surface, wherein the top load bearing surface and the bottom load bearing surface each include an opening allowing access to an interior of the frame;
    a rear surface having at least a portion that is opaque to X-rays attached between the top load bearing surface and the bottom load bearing surface and a front surface having at least a portion that is opaque to X-rays extending between the top load bearing surface and the bottom load bearing surface;
    a plate arranged along a plane (P), and attached to the front surface of the implant at a fixed angle, defining the front surface of the implant, the plate including a plurality of clearance holes for receiving a corresponding plurality of medical fasteners;
    and,
    two solid side surfaces extending between the front surface and the rear surface, each side surface including a solid side panel which has a portion that X-ray translucent encompassed by a portion that is opaque,
    wherein the top load bearing surface comprises a first frictional surface for applying frictional forces between the top load bearing surface and an adjacent bone surface; and the bottom load bearing surface comprises a second frictional surface for applying frictional forces between the bottom load bearing surface and an adjacent bone surface and wherein the top load bearing surface and the bottom load bearing surface between them form an axis of elongation (A) that is an intermediate axis between an elongated top load bearing surface and an elongated bottom load bearing surface, and wherein the plane (P) is at a non-right angle with respect to the axis of the elongation (A).

2. The inter-vertebral implant of claim 1, wherein:
    the non-right angle is approximately 86 degrees.

3. The inter-vertebral implant of claim 1, wherein:
    the non-right angle is approximately 82 degrees.

4. The inter-vertebral implant of claim 1, where the non-right angle is within a range of between 86 and 82 degrees.

5. The inter-vertebral implant of claim 1, wherein:
    the top load bearing surface and the bottom load bearing surface are each opaque to X-rays.

6. The inter-vertebral implant of claim 5, wherein said solid side panels are load bearing members constructed and arranged so that: said inter-vertebral implant with said solid side panels has a first strength; and said inter-vertebral implant without said solid side panels has a second strength; said first strength being from two to ten times greater than said second strength.

7. The inter-vertebral implant of claim 1, wherein:
    each solid side panel extends between the front surface and the rear surface, and extends between the top load bearing surface and the bottom load bearing surface.

8. The inter-vertebral implant of claim 1, wherein:
    a vertical distance between the top load bearing surface and the bottom load bearing surface is smaller at the rear surface than at the front surface.

9. The inter-vertebral implant of claim 1, wherein:
    said hollow frame is a hollow right prism-shaped frame.

10. The inter-vertebral implant of claim 9, wherein:
    said hollow right prism-shaped frame is a hollow isosceles trapezoidal right prism-shaped frame.

11. The inter-vertebral implant of claim 10: wherein said rear surface defines a first end of said hollow isosceles trapezoidal right prism-shaped frame; and wherein said front surface defines a second end of said hollow isosceles trapezoidal right prism-shaped frame, the second end being larger than the first end.

12. The inter-vertebral implant of claim 9, wherein the hollow prism-shaped frame is constructed from at least one biocompatible material.

13. The inter-vertebral implant of claim 12, wherein the at least one biocompatible material is selected from the group consisting of:
   metals selected from the group consisting of titanium, nickel, aluminum, nickel-titanium alloys, titanium-aluminum alloys, titanium-aluminum-vanadium alloys, and mixtures thereof;
   ceramics selected from the group consisting of alumina, zirconia, calcium oxides, calcium phosphates, and hydroxyapatite;
   polymers selected from the group consisting of polyethylene, polypropylene, polysulfone, and polyetheretherketone (PEEK);
   natural bone tissue; and
   synthetic bone.

14. The inter-vertebral implant of claim 12, wherein the at least one biocompatible material is selected from the group consisting of titanium, nickel-titanium alloys, titanium-aluminum alloys, titanium-aluminum-vanadium alloys, and mixtures thereof.

15. The inter-vertebral implant of claim 12, wherein the at least one biocompatible material is bone tissue harvested from an autologous source; allograft bone tissue; xenograft bone tissue, or artificial bone.

16. The inter-vertebral implant of claim 1, wherein the hollow frame is contrasted from a single biocompatible material selected from the group consisting of titanium, nickel-titanium alloys, titanium-aluminum alloys, and titanium-aluminum-vanadium alloys: and wherein said solid side panels are thinner than the front surface and the rear surface.

17. The inter-vertebral implant of claim 1, wherein the top load bearing surface, the bottom load bearing surface, the front surface, and the rear surface are constructed from a first biocompatible material; and
   the solid side panels are constructed from a second biocompatible material.

18. The inter-vertebral implant of claim 17, wherein:
   the first bio-compatible material is selected from the group consisting of titanium, nickel, aluminum, nickel-titanium alloys, titanium-aluminum alloys, titanium-aluminum-vanadium alloys, and mixtures thereof; and the second bio-compatible material is selected from the group consisting of:
ceramics selected from the group consisting of alumina, zirconia, calcium oxides, calcium phosphates, and hydroxyapatite
polymers selected from the group consisting of polyethylene, polypropylene, polysulfone, and polyetheretherketone (PEEK); and an X-ray transparent metal foil.

19. The inter-vertebral implant of claim 18, wherein:
   the X-ray transparent metal foil is an aluminum foil or a titanium foil.

20. The inter-vertebral implant of claim 17, wherein:
   the first bio-compatible material is selected from the group consisting of natural bone tissue or synthetic bone; and
   the second bio-compatible material is an X-ray transparent metal foil.

21. The inter-vertebral implant of claim 1, further comprising a bone grafting material in the interior of the frame.

22. The inter-vertebral implant of claim 1, wherein at least the top and bottom load bearing surfaces have been modified to support osteointegration.

23. The inter-vertebral implant of claim 1, wherein at least a portion of the top load bearing surface and at least a portion of the bottom load bearing surface are modified by etching or sandblasting to support osteointegration.

24. The inter-vertebral implant of claim 1, wherein:
   the hollow frame is made of titanium or an alloy thereof; and
   at least a portion of the top load bearing surface and at least a portion of the bottom load bearing surface are modified by coating with hydroxyapatite or tricalcium phosphate to support osteointegration.

25. The inter-vertebral implant of claim 1, wherein: said plurality of clearance holes comprising a plurality of indented offset screw holes; each medical fastener comprising a screw.

26. The inter-vertebral implant of claim 1, wherein:
   a first screw hole of said plurality of screw holes is adapted to direct a first screw into an upper vertebra, and
   a second screw hole of said plurality of screw holes is adapted to direct a second screw into a lower vertebra.

27. The inter-vertebral implant of claim 1, wherein:
   said first frictional surface is a photoetched portion of said top load bearing surface; and said second frictional surface is a photoetched portion of said bottom load bearing surface.

* * * * *